United States Patent [19]

Dragan

[11] 4,217,686

[45] Aug. 19, 1980

[54] ORTHODONTIC O-RING AND LIGATOR THEREFORE

[76] Inventor: William B. Dragan, R.F.D. #1 Burr St., Fairfield, Conn. 06430

[21] Appl. No.: 834,180

[22] Filed: Sep. 19, 1977

Related U.S. Application Data

[60] Division of Ser. No. 631,920, Nov. 14, 1975, Pat. No. 4,106,374, which is a continuation-in-part of Ser. No. 423,420, Dec. 10, 1973, abandoned.

[51] Int. Cl.$^2$ .............................................. B23P 17/00

[52] U.S. Cl. ........................................ 29/413; 81/302; 433/4; 433/13

[58] Field of Search ................. 32/66, 14 A; 206/820, 206/63.5, 338; 81/302; 225/97; 29/413

[56] References Cited

U.S. PATENT DOCUMENTS

| | | | |
|---|---|---|---|
| 1,428,357 | 9/1922 | Bullard | 81/416 |
| 1,810,631 | 6/1931 | Trump | 81/302 |
| 3,416,650 | 12/1966 | Mortensen | 206/338 |
| 3,530,583 | 9/1970 | Klein et al. | 32/14 A |
| 4,106,374 | 8/1978 | Dragan | 81/302 |

FOREIGN PATENT DOCUMENTS

| | | | |
|---|---|---|---|
| 1012132 | 4/1952 | France | 81/302 |

*Primary Examiner*—James L. Jones, Jr.
*Attorney, Agent, or Firm*—Arthur T. Fattibene

[57] ABSTRACT

The disclosure is directed to an orthodontic O-ring assembly which comprises a plurality of orthodontic O-rings integrally molded to a core which can be readily wrapped about an orthodontist's hand and the respective O-rings being individually dispensed by a ligator. The ligator comprises a tool having relatively moveable jaws which are sized so as to be received within the internal diameter of the O-ring in the closed position and thereafter moved to an open or expanded position to effect the stretching of the O-ring to be dispensed, thereby causing the O-ring to separate from its core at a frangible point. In a modified form of the invention, the ligator may be provided with a lock to maintain the ligator in the open jaw position.

7 Claims, 16 Drawing Figures

30

24

31

93
82B
92
90A
90
89
82
82A 93
82B
90
92
90A

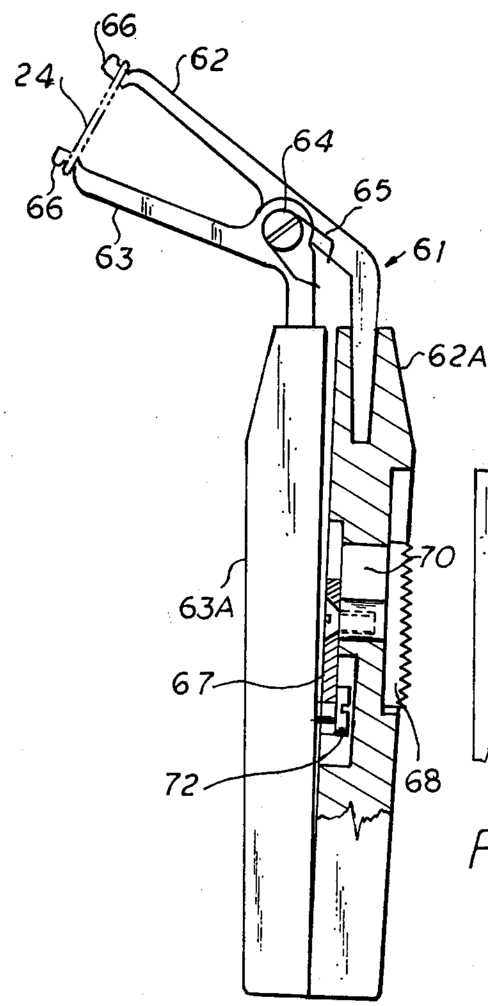
FIG. 14
FIG. 15
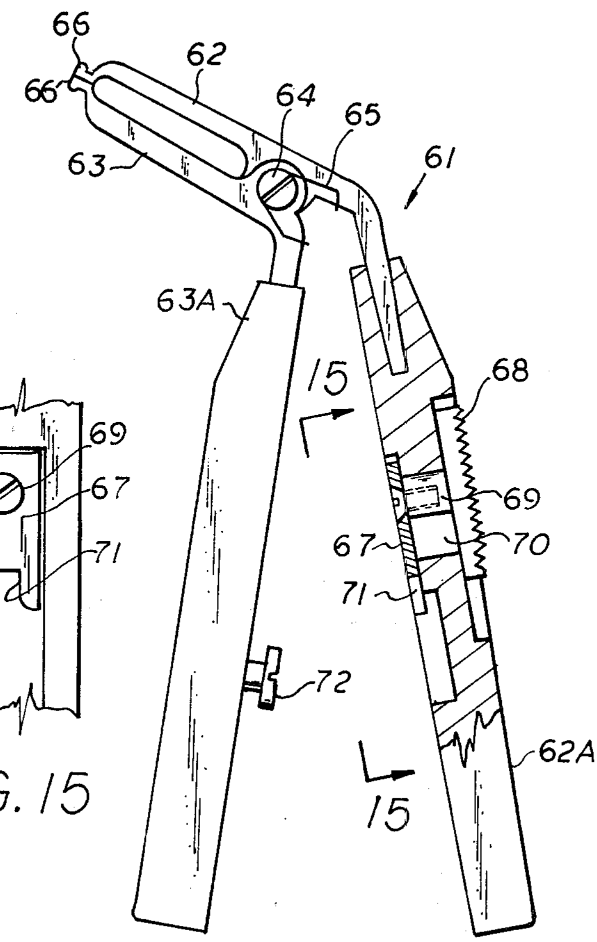
FIG. 13
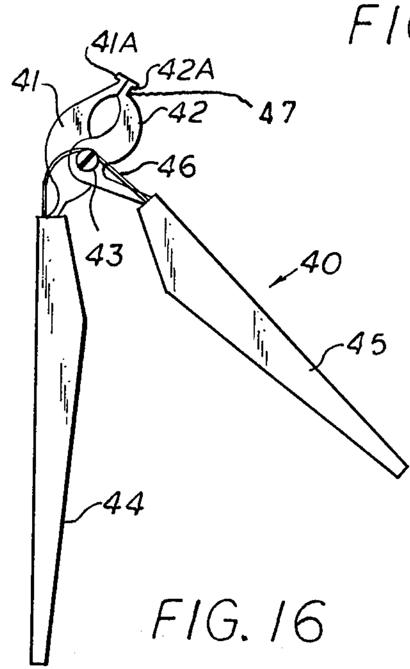
FIG. 16

ORTHODONTIC O-RING AND LIGATOR THEREFORE

RELATED APPLICATIONS

This application is a divisional application of a co-pending application Ser. No. 631,920 filed Nov. 14, 1975, now U.S. Pat. No. 4,106,374 for Orthodontic O-ring Dispenser and Ligator Therefor, which was a continuation in part application of Application Ser. No. 423,420 filed Dec. 10, 1973 now abandoned for Orthodontic O-Ring Dispenser and Ligator Therefor.

PROBLEM AND PRIOR ART

The esthetics of an orthodontic procedure have been greatly improved by the technique of adhereing directly to the patient's teeth a bracket, which may be formed of either metal or plastic and the attachment thereto of a resilient wire for exerting on the teeth the required force needed for straightening or shifting of the teeth as may be required during an orthodontic treatment. It is the present practice to utilize very small o-rings made of an elastic material for attaching the wire to the respective brackets.

Heretofore such O-rings were randomly packaged, and because of their size and randomly packaged arrangements considerable difficulty has been encountered in the handling and placing of such O-rings onto the brackets to hold the wire in place with respect thereto. The practice heretofore in placing such O-rings onto the teeth brackets generally consisted of the orthodontist "fishing" for the O-rings with a probe and with the use of such probe stretching the O-ring over the bracket to secure the wire. Such procedure was relatively primative, time consuming, and wasteful as many O-rings would be frequently dropped and lost in effecting the removal thereof from the box or source of supply and the placement thereof onto the patient's teeth bracket. As this technique of straightening teeth required the application of a relatively large number of such O-rings, it is readily apparent that the application of such O-rings is a tedious and time consuming task.

Objects

An object of this invention resides in the provision of an orthodontic O-ring assembly or manufacture which is simple in construction, which can be inexpensively manufactured and which is positive in operation.

Another object is to provide an orthodontric O-ring manufacture in which the O-rings can be readily dispensed and applied to a patient's mouth with the aid of a ligator.

Another object is to provide for an orthodontic O-ring assembly in which the plurality of individual O-rings are integrally molded as a unitary item in a manner whereby the respective O-rings can be individually dispensed.

Another object resides in the provision of a ligator for facilitating the dispensing and application of the O-ring to a patient's mouth.

BRIEF SUMMARY OF THE INVENTION

This invention is directed to a plurality of O-rings which are integrally connected or molded to a core or tree in a manner whereby the individual O-rings can be individually dispensed or removed from the core as desired by stretching the O-ring with a ligator. The ligator comprises a tool having relatively moveable jaws which are maintained normally closed and sized so as to be received within the internal diameter or hole of the O-ring to be dispensed. Upon the opening of the jaws, the O-ring is stretched or distorted to form a flat oval. In doing so, the stretching or distortion of the O-ring causes it to separate at a predetermined frangible point, and is positioned on the ligator so that the orthodontist can readily position the stretched O-ring onto the brace or bracket. In one form of the invention, the ligator is provided with a locking means for maintaining the ligator jaws in an open position.

In another form of the invention, the ligator is formed of complementary molded parts having a simplified jaw construction formed simply of wire inserts.

Features

A feature of this invention resides in the provision of an orthodontic O-ring manufacture in which the O-rings can be expeditiously dispensed in a minimum of time and with a minimum of effort.

Another feature of the invention resides in an orthodontic O-ring manufacture in which the O-rings can be individually dispnesed with the aid of a ligator in a manner wherein the O-ring upon being dispensed is in position on a tool which is readied for direct application of the O-ring to the patient's mouth.

Another feature resides in the provision of an improved ligator for facilitating the removal of the O-ring from its supply and the placement of the O-ring onto the bracket attached to a patient's tooth.

Another feature of the invention resides in the provision wherein the orthodontic O-rings manufacture is one in which the O-rings are integrally formed.

Other features and advantages will become more readily apparent when considered in view of the drawings and specification in which:

FIG. 13 is a side view of a modified ligator construction for effecting the removal of the O-ring and for applying the O-ring to a patient's mouth.

FIG. 14 is a side elevation of the ligator shown in FIG. 6 but illustrated in the latched or locked position.

FIG. 15 is a fragmentary detailed view taken along lines 15—15 on FIG. 12.

FIG. 16 is another modified embodiment.

DETAILED SPECIFICATION

Figure 1:
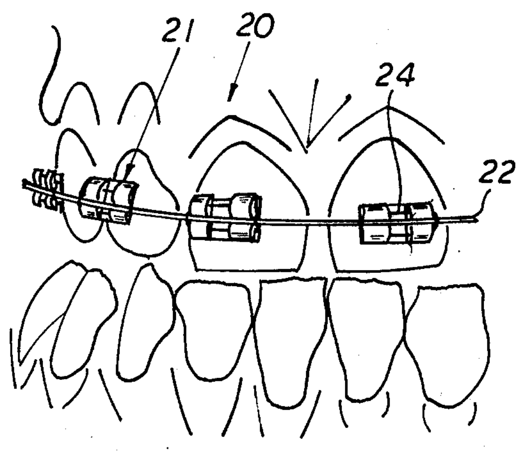
FIG. 1 is a perspective view of teeth braces illustrating how an orthodontic o-ring is applied to a patient's teeth brace.
Figure 2:
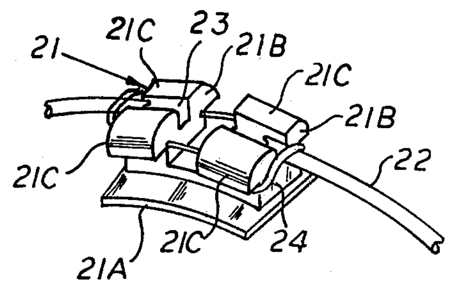
FIG. 2 is a detailed fragmentary perspective view illustrating an orthodontic O-ring as applied to a patient's teeth brace.

Referring to the drawings there is shown in FIG. 1 an orthodontic brace 20 for straightening and/or shifting patient's teeth which comprises a bracket 21 which is bonded directly to each tooth and through which a resilient tensioning wire 22 is strung for tying the respective teeth together. The bracket 21 is firmly attached to a tooth by a suitable adhesive. As best seen in FIG. 2, the bracket 21 comprises a mounting plate 21A which has projecting forwardly therefrom a pair of lugs 21B having oppositely turned ear portions 21C. Extending trasversely of the respective eared lugs 21B is a groove 23 for receiving the tensioning wire 22. To secure or attach the tensioning wire 22 within the groove 23 of the projecting lugs 21B, it is customary to utilize very small elastic O-rings 24. As best seen in FIG. 2, the attachment of the wire 22 to the respective teeth brackets 21 is achieved by stretching and looping the O-rings 24 around the projecting lugs 21B so that the wire is maintained in the groove 23 of the bracket in the manner shown in FIG. 2.

Figure 3:
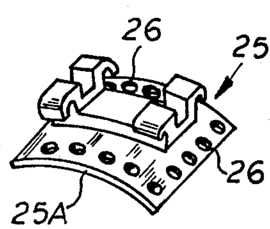
FIG. 3 illustrates a modified bracket construction.

The bracket 25 of FIG. 3 is similar to that of FIG. 2 except that it is formed of a metallic material whereas the bracket construction of FIG. 2 is formed of a plastic material. For this reason the mounting plate 25A of the bracket of FIG. 3 is provided with a series of spaced openings 26 to provide a means whereby the bonding adhesive may flow therethrough to effect a more secure bond of the metallic bracket to a patient's tooth. In all other respects the construction of the metallic bracket 25 of FIG. 3 is similar to that of FIG. 2.

Figure 4:
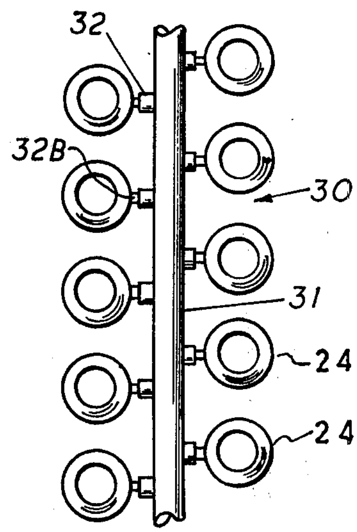
FIG. 4 is a view of the integrally molded orthodontic O-ring embodying the invention.
Figure 5:
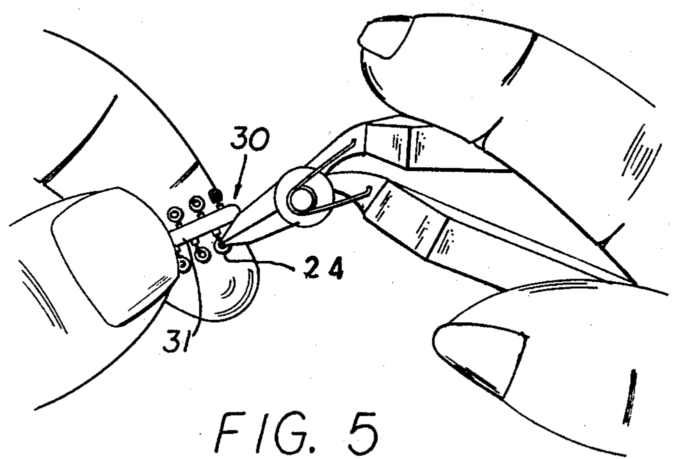
FIG. 5 illustrates the manner in which an orthodontist may utilize the O-rings of FIG. 4.

Because it was heretofore difficult to apply the O-ring to the bracket 21 or 25 secured to a patient's tooth because of the smallness of the respective O-rings and the manner in which they were packaged, there is provided in accordance with this invention an improved orthodontic O-ring assembly whereby the placement of the O-ring onto the teeth bracket is greatly facilitated. Referring to FIG. 4, there is shown an O-ring assembly or manufacture 30 which comprises a core or tree 31 to which there is connected a plurality of orthodontic O-rings 24. Each O-ring 24 is connected to its core 31 by a web or branch 32. As shown, the web or branch 32 is provided with a weakened or frangible portion 32B located adjacent the outer circumference of the associated O-ring 24. The O-rings 24, the connecting web 32 and associated core 31 are integrally molded of the same elastic material as a unitary member. It will be understood that the tree 31 may be of any preferred length. With the arrangement described, the O-rings are connected until dispensed.

With the construction described, an orthodontist can wrap an O-ring tree 31 about his finger or hand as he separates the respective O-rings from its tree 31 by a ligator as will be hereinafter described. To effect a dispensing of the O-rings 24 from its tree 31, the orthodontist need only insert the nose of tip portion of a ligator, to be described, into the hole of a given O-ring; and by compressing the handles of the ligator effects the opening of the jaw tips, the engaged O-ring is stretched to form a flat oval which causes the O-ring to separate from the stem 31 at the frangible or weakened portion 32B.

Figure 6:
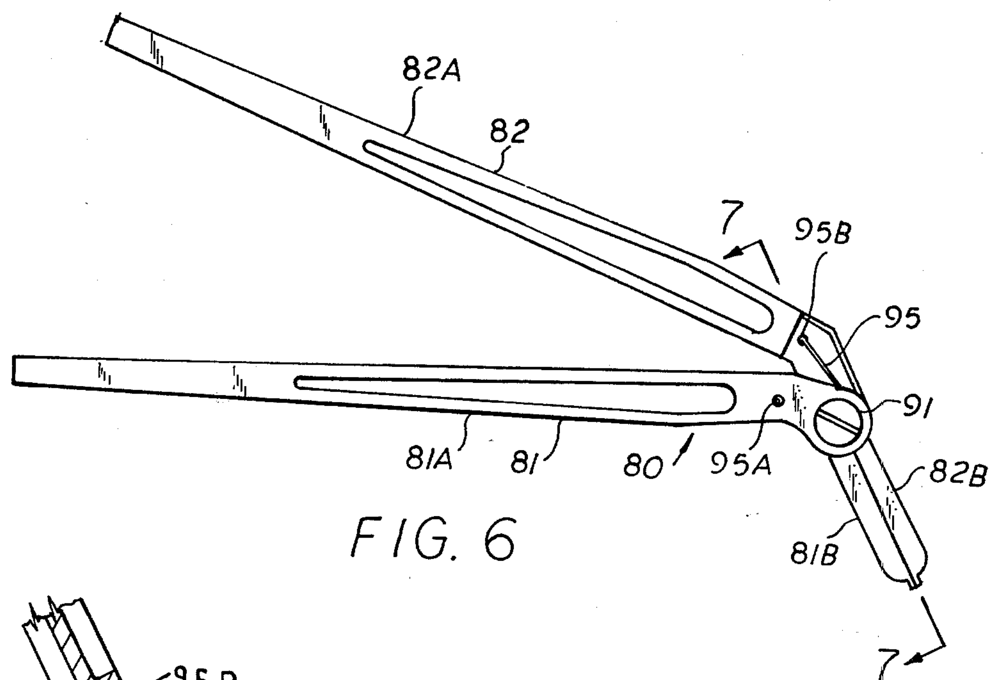
FIG. 6 is a side view of a ligator embodying the invention.

Thus the dispensing arrangement of F gure 4 enables the plastic O-rings 24 to be integrally molded onto a connecting stem or tree in a manner whereby the individual o-rings can be readily successively dispensed upon the dentist's effecting a stretching of the required O-ring with the ligator of the type described with respect to either FIGS. 6, 13 or 16.

In the form of the invention as shown in FIG. 4, it will be understood that the number of O-rings which can be integrally molded to a single core 31 may be varied as may be considered practical. Also the stem or tree is made sufficiently long so that the tree can be readily wrapped about the dentist's hand so as to be readily accessible and thereby facilitates the picking off of the necessary O-rings as required by the dentist. Since the tree is formed of a readily flexible elastic material, it can be easily wrapped or flexed about the dentist's hand or finger when needed.

The orthodontic O-rings 24 to which this invention relates comprise of relatively small esalstic O-rings which have an outside diameter of approximately 3 to 4 millimeters. Because of their extremely small size the handling thereof has been difficult. The dispensing tree herein described has been used to greatly facilitate the handling and application of these small orthodontic O-rings.

Figure 9:
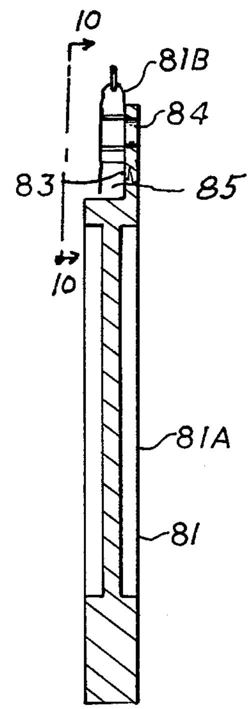
FIG. 9 is a sectional view of lever of FIG. 8 taken along line 9—9 thereof.
Figure 8:
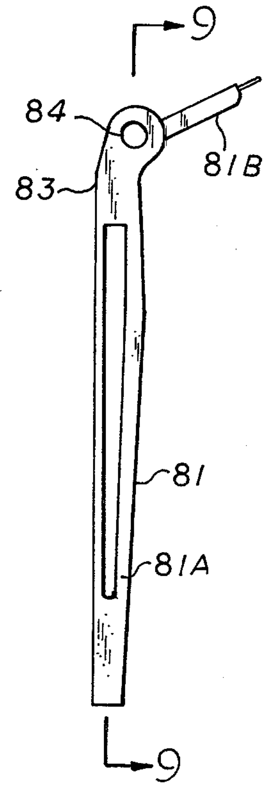
FIG. 8 is a detail plan view of one lever component of the ligator of FIG. 6.
Figure 10:
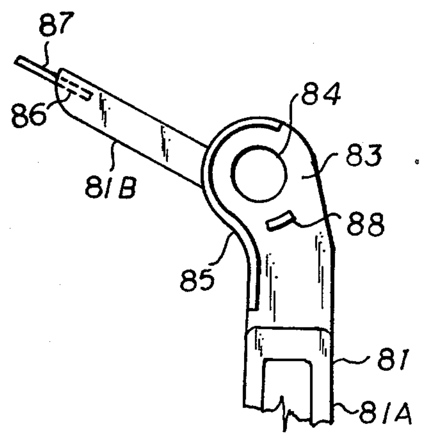
FIG. 10 is an auxiliary view taken along line 10—10 on FIG. 9.

Referring to FIGS. 6 to 12, there is shown a ligator construction by which the separation of the O-rings 24 from its tree 21 and the application thereof to a brace 20 is effected. As best seen in FIG. 6, the ligator 80 comprises a pair of levers 81 and 82. Each lever 81 and 82 comprise a handle portion 81A, 82A and a jaw holding portion 81B, 82B respectively. Referring to FIGS. 9 and 10, it will be noted that the handle portion 81A of lever 81 adjacent the jaw end comprises a reduced section as at 83 which terminates in a slightly offset jaw holding portion 81B. Adjacent the end of the reduced portion there is provided a hole 84. Circumscribing a portion of the hole 84 and extending along the outer portion of the reduced section 83 is a laterally extending flange 85. In accordance with this invention, the jaw holding portion 81B is provided with a bore 86 in the top end thereof into which there is inserted a wire to define a jaw tip 87.

Formed integral on the reduced portion 83 is a projection 88 which functions as a spacer and bearing point between the two levers 81 and 82.

Figures 11, 12:
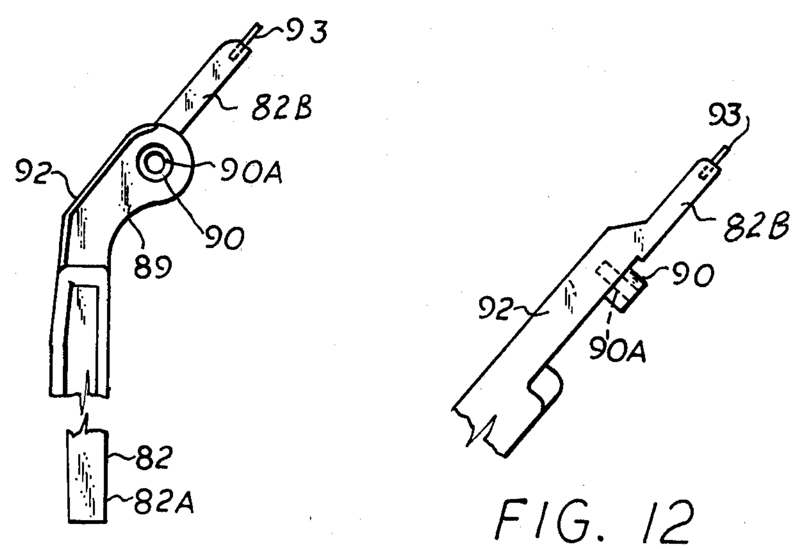
FIG. 11 is a detail plan view of the other lever component of the ligator of FIG. 6.
FIG. 12 is a fragmentary top view of FIG. 11.

The handle portion of lever 82 is also provided with a reduced portion 89 to complement the reduced portion 83 of lever 81. As best shown in FIGS. 11 and 12, the reduced portion 89 has extending laterally thereof a boss 90 which in the assembled position is adapted to be received in the mating hole 84 of lever 81. The boss 90 is provided with a hole 90A which is adapted to receive a screw fastener 91 as will be hereinafter described. The outer edge portion of the reduced section 89 has extending therealong a lateral flange 92 which complements flange 85 of handle portion 81B. The projecting jaw holding portion 82 B is provided with a bore in which a jaw wire 93 is inserted. Thus jaws wires 87 and 93 define complementary jaw tips which are sized so as to be readily received in the hole or internal diameter of O-rings 24.

Figure 7:
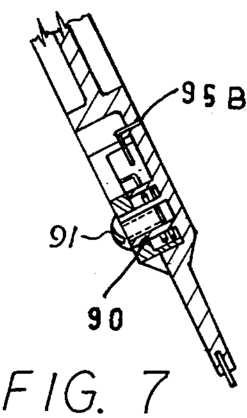
FIG. 7 is a sectional view taken along line 7—7 on FIG. 6.

A spring means 95 is provided for normally biasing the jaw tips 87 and 93 toward the closed position as seen in FIG. 6. Referring to FIG. 7, the spring means comprises a pigtail spring having its coiled portion looped about the boss 90 of lever 82 in the assembled position. One end 95A of spring 95 is anchored in a hole formed in lever 81. The other end 95B is anchored in a hole formed in lever 82.

To assemble the ligator 80 of FIG. 6, the two levers are disposed in mating position as seen in FIGS. 6 and 7, with the spring 95 coiled about boss 90. Upon anchoring the ends 95A and 95B of the spring 95 to its respective handle portion, the assembly is secured by a screw fastener 91 which may be a self-trapping screw.

It will be understood that the respective levers can be readily molded of a suitable plastic material. The wire jaw tips thus provide the ligator with a sturdy jaw tip which has the sufficient strength needed to stretch the O-rings in preparation to placing the rings 24 onto the teeth braces.

To effect the separation of the O-rings 24 from its tree, the orthodontist need only to wrap the tree 21 about his finger or hand, and with the other hand simply insert the tips 87, 93 into the hole of the O-ring and compress the handle portions to open or spread the tips 87 and 93. In doing so the O-ring is stretched to a flat oval whereby the stretching thereof also effects or facilitates the separation of the given O-ring from its branch or web at the weakended point.

With the O-ring separated and the O-ring stretched in the tips of the ligator, the O-ring 24 is in position whereby it can be readily applied by the orthodontist to the patient's braces. Thus the separation and application of the O-ring can be achieved in one continuous motion, which results in greatly expediting the orthodontric procedure.

FIG. 16 discloses a modified embodiment of a ligator. The ligator 40 of this embodiment comprises a tool having relatively moveable jaw members 41 and 42 which are pivotally connected for movement between an open and a closed position about a pivot 43. As best seen in FIG. 16, a handle portion 44 and 45 is connected to each of the respective jaw members 41 and 42. A spring 46 is coiled about the pivot 43 and has its free ends operatively connected to the respective handles 44 and 45. Spring 46 thus normally biases the jaw members 41, 42 to a normally closed position as is indicated in FIG. 16.

In accordance with this invention, the respective jaw members 41 and 42 as seen in FIG. 16 are each provided with a nose or tip portion 41A and 42A respectively. In the closed position, the respective nose or tip portions 41A and 42A are disposed in abutting relationship. The endmost tip of the respective nose portions 41A and 42A of the respective jaw members 41 and 42 are provided with an outwardly turned nib to define a hook 47, which in the open position of the jaws will function to retain an O-ring 24 thereon. In the closed position, the nose portions 41A and 42A of jaws 41 and 42 respectively form a needle like projection which can be readily received within the internal diameter or hole of an O-ring. Upon compressing the respective handles 44 and 45 of the ligator 40 with the jaws inserted into the hole of an O-ring, the jaws are spread open so that the end ring engaged thereby is stretched to define a flat oval position. By stretching the O-ring to this flat oval position, the O-ring can be readily separated from its tree.

FIGS. 13, 14 and 15 illustrate another modified form of ligator construction. In this form of the invention, the ligator comprises a pair of jaw members 62, 63 which are pivoted for relative movement with respect to one another about a pivot pin 64. Connected to the extended end of the respective jaw members 62, 63 is a handle portion 62A, 63A, a spring means 65, which is pigtailed about the pivot pin 64 and has its free ends in bearing relationship to the respective jaw members 62, 63 so as to normally bias the jaws to the closed position, as best seen in FIG. 13. The respective jaw members 62, 63 are each provided with a nose portion 66 similar to that hereinbefore described with respect to the ligator 40 of FIG. 16.

In the ligator construction 61 of FIGS. 13 and 14, a latching or locking means is provided for maintaining the jaws 62, 63 in the spread or open position, as indicated in FIG. 14. As best seen in FIGS. 13 and 14, the locking means comprises a slide latch 67 which is recessed on the inner side of one of the handle members, e.g., 62A. The slide latch 67 is operatively connected to a slide actuator 68 which is recessed in the opposite surface portion of a handle 62A, the slide actuator 68 being connected to the sliding latch 67 by a suitable connector, as for example, a screw or the like 69. As seen in FIGS. 13 and 14 the connector is moveably mounted in a slot 70 formed in handle 62A to define the limits of movement of the latch 67.

As best seen in FIG. 15, the slide latch 67 is provided with a cut-out portion to define a notch 71 which is adapted to receive or latch onto a catch 72 which is mounted on the contiguous side of the other handle member 63A

In the illustrated form of the invention as shown in FIG. 13, the catch 72 comprises a headed screw of like fastener. By actuating or sliding the slide latch 67 to the position illustrated in FIG. 14 when the handles are compressed, it will be noted that notch 71 of the slide latch 67 will engage the catch 72. So long as the slide latch 67 is engaged with the catch 72, the jaw members 62, 63 of ligator 61 will be maintained in an open position as indicated in FIG. 13.

To effect the closing of the jaws, the actuator 68 is simply shifted to the opposite position whereupon the notch 71 of slide latch 67 becomes disengaged from the catch 72. In the event that the dentist is interrupted in or during an orthodontic treatment, the ligator described with respect to FIGS. 13 and 14 may be set to its locked position until such time that the orthodontic treatment can be resumed.

From the foregoing, it will be noted that the dispensing assembly of FIG. 4 enables the elastic O-rings 24 to be integrally molded onto a connected stem or tree in a manner whereby the individual o-rings can be readily successively dispensed upon the dentist or orthodontist effecting the stretching of the selected O-ring with the ligator of the type described with respect to either FIGS. 6, 13 or 16.

In the form of the invention as shown in FIG. 4, it will be understood that the number of O-rings which can be integrally molded to a single core or stem may be varied as may be considered practical. Also, the stem or tree is made sufficiently long so that the tree can be readily wrapped about a portion of one's hand whereby the O-rings are rendered readily accessible and to facilitate the picking off of the desired O-ring as might be required.

It is to be noted that the orthodontic O-rings 24 to which this invention relates, comprises a relatively small elastic O-ring which has an outside diameter of approximately 3 to 4 millimeters. Because of their extremely small size, the handling thereof has been heretofore difficult. The dispensing tree herein described will therefore greatly facilitate the handling and application of these very small orthodontic elastic O-rings to the patient's braces.

From the foregoing, it will be apparent that the dispensing and application of the O-rings to a tooth bracket or brace during an orthodontic treatment is greatly simplified in that the dispensing operation and subsequent placement of the O-ring onto the tooth bracket can be effected in a simply continuos motion thereby saving the orthodontist considerable time and effort.

While the instant invention has been described with respect to particular embodiments thereof, it will be readily understood and appreciated that variations and modifications may be made without departing from the spirit or scope of this invention.

What is claimed is:

1. An orthodontic O-ring assembly comprising:
an elongated flexible core adapted to be wrapped about a portion of an orthodontist's hand,
a plurality of minature elastic, orthodontic O-rings,
a readily frangible web connecting each of said O-rings to said core at spaced apart intervals therealong,
said frangible web having a weakened portion adjacent the circumference of the attached O-ring,
said elastic O-ring, core and frangible webs being integrally formed as a unitary casting of the same material, and
means for effecting the distortion of an O-ring to define a flat oval whereby said distortion enables the separation of said distorted O-ring from its respective web at said weakened portion.

2. The assembly as defined in claim 1 wherein said latter means comprises:
a ligator having a pair of relatively moveable levers, each of said levers terminating in a jaw tip,
means for pivotally connecting said levers for pivoting said tips between an open and closed position,
means for normally biasing said jaw tips toward a closed position whereby said jaw tips are contiguously disposed in the closed position.

3. The assembly as defined in claim 2 and including a jaw holding portion wherein said respective jaw tips comprise a wire insert connected to and projecting beyond the end of the respective jaw holding portion, said wire insert in the normally closed position of said jaw holding portion being of a size adapted to be readily received within the internal diameter of an O-ring.

4. A ligator comprising:
a pair of jaw members,
pivot means for pivotally connecting said jaw members for relative movement between a normally closed position and an open position,
each of said jaw members having a nose portion which in the closed position can be readily received within the internal diameter of an O-ring,
each of said nose portions having an outwardly turned hook for holding an O-ring in the stretched position when said jaws are in the opened position,
a handle connected to each jaw member,
and means on said handle for locking said jaw members in open position thereof,
wherein said locking means includes a sliding latch slideably mounted on one of said handles,
and a complementary catch mounted on the other handle,
and a slide actuator connected to said latch for sliding said latch between the locked and unlocked position thereof.

5. An orthodontic o-ring assembly comprising an elongated flexible core which is adapted to be wrapped about a portion of an orthodontist's hand,
a plurality of minature elastic orthodontic o-rings,
a plurality of branches connected to said core, said o-rings being connected to free end of said branches,
each of said branches having a weakened portion adjacent the circumference of the attached o-ring,
said elastic o-ring core and connecting branches being integrally formed as a unitary member of the same elastic material whereby distortion of said o-ring to define a flat oval facilitates the separation of said o-ring from its associated branch at said weakened portion.

6. The invention as defined in claim 5 wherein said o-rings have an outside diameter of at least 3 to 4 millimeters.

7. A method of dispensing dental O-rings comprising the steps of: forming a core member of an elastic material so as to define an elongated central core, having spaced therealong, a plurality of branches, and forming an O-ring at the end of each of said branches of the same elastic material as the material of the core and connected branches, forming each of said branches with a frangible portion, and effecting the separation of the O-ring from its associated branch at the formation of the frangible portion by distorting the O-ring to a flat oval.

* * * * *

REEXAMINATION CERTIFICATE (524th)

United States Patent [19]

[11] B1 4,217,686

Dragan

[45] Certificate Issued Jun. 24, 1986

[54] ORTHODONTIC O-RING AND LIGATOR THEREFORE

[75] Inventor: William B. Dragan, Fairfield, Conn.

[73] Assignee: Modcom Inc., Canby, Oreg.

Reexamination Request:
No. 90/000,878, Oct. 7, 1985

Reexamination Certificate for:

| | |
|---|---|
| Patent No.: | **4,217,686** |
| Issued: | **Aug. 19, 1980** |
| Appl. No.: | **834,180** |
| Filed: | **Sep. 19, 1977** |

Related U.S. Application Data

[60] Division of Ser. No. 631,920, Nov. 14, 1975, Pat. No. 4,106,374, which is a continuation-in-part of Ser. No. 423,420, Dec. 10, 1973, abandoned.

[51] Int. Cl.[4] .............................................. B23P 17/00

[52] U.S. Cl. ........................................ 29/413; 81/302; 433/4; 433/13

[58] Field of Search ............................ 433/11; 81/302

[56] References Cited

U.S. PATENT DOCUMENTS 3,193,094 7/1965 Shulstad .

*Primary Examiner*—James L. Jones, Jr.

[57] ABSTRACT

The disclosure is directed to an orthodontic O-ring assembly which comprises a plurality of orthodontic O-rings integrally molded to a core which can be readily wrapped about an orthodontist's hand and the respective O-rings being individually dispensed by a ligator. The ligator comprises a tool having relatively moveable jaws which are sized so as to be received within the internal diameter of the O-ring in the closed position and thereafter moved to an open or expanded position to effect the stretching of the O-ring to be dispensed, thereby causing the O-ring to separate from its core at a frangible point. In a modified form of the invention, the ligator may be provided with a lock to maintain the ligator in the open jaw position.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * *